United States Patent [19]

Westerterp

[11] Patent Number: 4,731,387

[45] Date of Patent: Mar. 15, 1988

[54] PROCESS FOR CARRYING OUT A CHEMICAL EQUILIBRIUM REACTION

[75] Inventor: Klaas R. Westerterp, Enschede, Netherlands

[73] Assignee: Shell Oil Company, Houston, Tex.

[21] Appl. No.: 907,422

[22] Filed: Sep. 15, 1986

[30] Foreign Application Priority Data

Sep. 30, 1985 [GB] United Kingdom ................. 8524025

[51] Int. Cl.$^4$ .............................................. C07C 27/06
[52] U.S. Cl. .................................. 518/706; 518/713; 518/722; 518/728
[58] Field of Search ................ 518/713, 722, 728, 706

[56] References Cited

U.S. PATENT DOCUMENTS

| | | |
|---|---|---|
| 2,473,129 | 6/1949 | Atwell . |
| 2,542,521 | 2/1951 | Hebshman et al. .................. 518/722 |
| 2,628,933 | 2/1953 | Eagle et al. .......................... 518/722 |
| 2,887,365 | 5/1959 | De Rycker et al. ................. 518/712 |
| 4,559,207 | 12/1985 | Hiller .................................. 518/713 |

FOREIGN PATENT DOCUMENTS 27329  4/1981  European Pat. Off. .

OTHER PUBLICATIONS

Roes, Thesis "The Behavior of a Gas-Solid Packed Column at Trickle Flow", (1978), p. 46.
Roes et al, Chemical Engineering Science, vol. 34, pp. 131–133, 1979.

*Primary Examiner*—Howard T. Mars
*Attorney, Agent, or Firm*—Ronald R. Reper

[57] ABSTRACT

In a process for carrying out a chemical equilibrium reaction by introducing gaseous starting compounds in a reaction zone containing a fixed bed of coarse catalyst particles having interstices between them, fine particles adsorbing substantially all of the product compounds are passed downwardly through the interstices and subsequently withdrawn from the reaction zone.

2 Claims, No Drawings

PROCESS FOR CARRYING OUT A CHEMICAL EQUILIBRIUM REACTION

BACKGROUND OF THE INVENTION

The invention relates to a process for carrying out a chemical equilibrium reaction by introducing one or more reactants in the gaseous phase into a reaction zone comprising one or more fixed beds of catalyst particles having interstices therebetween, at least a portion of said catalyst particles comprising a catalyst for said chemical equilibrium reaction.

In order to increase the product yield it is desirable to remove the product from the reaction zone effluent and to recycle unconverted starting compounds to the reaction zone. According to a method known from European patent specification No. 0 027 329 this is effected by condensing the product on cooling surfaces. However, in those cases where the position of the equilibrium reaction is unfavorable at the temperature at which the reaction is carried out the products of the equilibrium reaction will have a low concentration in the reaction mixture. In such cases cooling surfaces must be very large and have a relatively low temperature. Furthermore, the cooling surfaces simultaneously cool the unconverted reactants, so that much reheating is required before they can be recycled to the reaction zone. Moreover, the amounts of unconverted starting compounds to be recycled are usually very large, requiring substantial compression energy.

It is an object of the present invention to avoid recycling of unconverted reactants and to avoid using the cooling surfaces as described hereinbefore.

SUMMARY OF THE INVENTION

Accordingly, the invention provides a process for carrying out a chemical equilibrium reaction by introducing one or more reactants in the gaseous phase into a reaction zone comprising at least one fixed bed of catalyst particles, said catalyst particles having interstices therebetween, and at least a portion of said catalyst particles comprising a catalyst for said chemical equilibrium reaction, which process comprises passing in a downward direction through said interstices relatively fine particles, adsorbing substantially all of the product compound or product compounds of said chemical equilibrium reaction, and subsequently withdrawing said relatively fine particles from said reaction zone.

DESCRIPTION OF PREFERRED EMBODIMENTS

In the process according to the present invention the relatively fine particles are fine, i.e. of sufficiently small size with respect to the interstices between the catalyst particles, so that they are readily passed downwardly through the interstices of the catalyst particles and adsorb the reaction product or products immediately after release thereof from the surface of the catalyst. In this manner, the thermodynamic equilibrium is not reached and a high driving force for the reaction is maintained. Hence, the rate of reaction will remain high all over the length of the fixed bed or beds, which allows i.e., enables the use of fixed beds having a smaller volume than conventionally applied for the reaction. The reaction zone has one outlet only, viz, at the bottom for the relatively fine particles loaded with the product compound or compounds, no unconverted reactants being withdrawn from the reaction zone. In this manner, the reactants are completely converted in a single-pass operation and the products are adsorbed on the relatively fine particles.

Another feature of the present invention is that, where the equilibrium reaction is strongly exothermic, the relatively fine particles also take up heat from the reaction zone, thus preventing overheating the catalyst particles and avoiding an undesired rise of temperature. Temperatures over a cross-section of the fixed bed are equilibrated and heat transfer to the wall of the reaction zone is improved. Conditions can be selected by those skilled in the art in such a way that all heat of reaction is taken up by the relatively fine particles.

The reactants may be introduced into the reaction zone so that they flow upwardly, downwardly or laterally through the fixed bed or beds. Very good results have been obtained by introducing the reactants, with a suitable superficial velocity, into the reaction zone at the bottom of the fixed bed or at the bottom of the bottom fixed bed if two or more fixed beds positioned in series and on top of each other are used. In such a case the reactants flow upwardly through the fixed bed or beds. The upward superficial velocity of the gaseous reactants should not be too high, but should enable the relatively fine particles to pass down through the fixed bed countercurrently to the gasflow. If desired, the reaction mixture may be cooled, suitably indirectly between two consecutive fixed beds, or via the wall of the reactor.

The reaction zone is continuously fed at the top with relatively fine particles. These particles flow through the interstices between the catalyst particles of the fixed bed, usually in the form of trickles which are evenly distributed over the whole cross-section of the fixed bed. In order to prevent clogging the void fraction of the fixed bed should be sufficiently great to allow the relatively fine particles to trickle downwards through the interstices. The catalyst particles may have any suitable shape; they may, for example, be cylinders, Raschig rings, spheres or trilobes. The largest dimensions of the relatively course particles is suitably between 0.1 and 5 cm.

Examples of equilibrium reactions are:

(1) the manufacture of methanol according to the equation

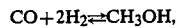
$$CO + 2H_2 \rightleftharpoons CH_3OH,$$

(2) the manufacture of ammonia according to the equation

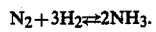
$$N_2 + 3H_2 \rightleftharpoons 2NH_3.$$

Very good results have been obtained with the manufacture of methanol from carbon monoxide and hydrogen in the presence of copper on a carrier. This process is suitably carried out at a temperature in the range of from 210° C. to 280° C. and a pressure in the range of from 25 to 200 bar. The relatively fine particles which may be used in the process suitably comprise silica-alumina having a largest dimension in the range of from 10 to 500 μm and a surface area in the range of from 10 to 500 m²/g.

The following examples further illustrate the invention.

The experiments were carried out in three identical, vertically positioned, cylindrical reactors, placed in series and on top of each other. A cooler for indirect cooling was installed between the top reactor and the middle reactor and one between the middle reactor and the bottom reactor. The top of the top reactor was provided with a gas outlet. Each reactor was surrounded by an electrically heated oven, had an internal diameter of 2.5 cm and was packed over a height of 50 cm with a mixture of copper catalyst particles and glass Raschig rings having a number ratio of catalyst particles to Raschig rings of 2:1. The catalyst contained 30% by weight of copper on a carrier and is sold by BASF under the trade name "S3-85". The catalyst particles were cylinders having a diameter of 0.5 cm and a height of 0.5 cm and the Raschig rings had a height of 0.7 cm, and outside diameter of 0.7 cm and a wall thickness of 0.1 cm. The void fraction of the packing was 0.581. The total weight of the catalyst particles present in the three reactors was 272 g.

A gaseous mixture containing carbon monoxide and hydrogen in a volume ratio CO to $H_2$ of 0.5 and prepared by mixing a gas having a CO content of more than 99.5% by volume with a gas having a hydrogen content of more than 99.9% by volume, was preheated and introduced into the bottom reactor below the packing thereof. A stream of amorphous silica-alumina particles was introduced into the top of the top reactor, was allowed to trickle downwardly through the three catalyst beds and the two coolers placed between the reactors, was withdrawn from the bottom of the bottom reactor, was cooled indirectly and was received in a storage vessel. The particles consisted of 87% by weight of silica and 13% by weight of alumina, had a particle density of 813 kg/$m^3$, a skeletal density of 2200 kg/$m^3$ and an average particle diameter of 90 um. The surface area distribution of the pores was as follows (measured according to the B.E.T. method as described in "Catalysis", Volume 1, edited by Paul H. Emmett, 1954, pages 36–42):

| pore diameter range nm | surface area $m^2/g$ |
|---|---|
| 2.0–3.0 | 92.6 |
| 3.0–4.0 | 101 |
| 4.0–5.0 | 138.1 |
| 5.0–6.0 | 89.2 |
| 6.0–7.0 | 38.4 |
| 7.0–9.0 | 31 |
| 9.0–13.0 | 10 |

EXAMPLE

An experiment was carried out as described hereinabove with the gas outlet at the top of the top reactor being closed. The temperature of the three catalyst beds was maintained at 240° C. and the starting total pressure was 51 bar. The silica-alumina particles were introduced into the top reactor at a rate of 0.905 kg/h. After the introduction of these particles the pressure in the reactor started to decrease, methanol being adsorbed on the particles. Then, the rate of supply of the mixture of carbon monoxide and hydrogen was adjusted so as to maintain a total pressure of 51 bar in the reactor; in this manner a total of 3.24 mol of carbon monoxide and hydrogen per hour was supplied in steady-state operation. An analysis of the methanol content of the silica-alumina collected in the storage vessel showed that the silica-alumina had adsorbed all the methanol formed, methanol being produced in an amount of 1.07 mol per ton of catalyst per s.

COMPARATIVE EXPERIMENT A

An experiment was carried out with an open gas outlet at the top of the top reactor, so that the unconverted gas and the methanol not adsorbed on the silica-alumina particles could leave the top reactor. The reactors were in a steady-state operation at a temperature of 236° C., a total pressure of 62.8 bar, a silica-alumina flow of 0.800 kg/h and a rate of supply of the mixture of carbon monoxide and hydrogen of 6.59 mol/h. An amount of 2.10 mol/h of gas was withdrawn through the gas outlet at the top of the top reactor; this gas contained 30% by volume of CO. The conversion of carbon monoxide was 71% and 0.07 mol of methanol per ton of catalyst per s was withdrawn from the top of the top reactor. The silica-alumina collected in the storage vessel contained 1.30 mol of methanol per ton of catalyst per s, the total rate of methanol production being 1.37 mol per ton of catalyst per s.

Comparison with the Example shows that all of the carbon monoxide and hydrogen that had been introduced into the reactor had been converted into methanol, so that no gas had to be recycled in the Example, whilst about 32% of the carbon monoxide and hydrogen supplied to the reactor had to be recycled in this Comparative Experiment.

COMPARATIVE EXPERIMENT B

Comparative Experiment A was modified by deleting the stream of silica-alumina particles. The conversion of carbon monoxide was only 42% and the total rate of methanol production was 0.92 mol per ton of catalyst per s.

I claim:

1. Process for carrying out a chemical equilibrium reaction by introducing as reactants carbon monoxide and hydrogen in the gaseous phase into a reaction zone comprising at least two vertically aligned fixed beds of catalyst particles suitable for converting said reactants into methanol positioned in series on top of each other, said catalyst particles having interstices therebetween, and at least a portion of said catalyst particles comprising a catalyst for said chemical equilibrium reaction, which process comprises introducing said reactants at the bottom of the bottommost bed to flow upwardly through the beds, passing in a downward direction through said interstices relatively fine particles, adsorbing substantially all of the product compound or product compounds of said chemical equilibrium reaction onto said particles, and subsequently withdrawing said relatively fine particles from said reaction zone.

2. Process as in claim 1, wherein said fine particles prior to passing through said interstices are at a temperature below the temperature within said reaction zone so that when passing through said interstices said fine particles take up heat from the reaction zone.

* * * * *